United States Patent [19]

Young et al.

[11] Patent Number: 4,776,326

[45] Date of Patent: Oct. 11, 1988

[54] MODULAR LOWER LIMB BRACING SYSTEM

[75] Inventors: David E. Young, Watlington; Kenneth P. Davis, Hillingdon, both of England

[73] Assignee: Protectair Ltd., England

[21] Appl. No.: 882,597

[22] Filed: Jul. 7, 1986

[30] Foreign Application Priority Data

Jul. 9, 1985 [GB] United Kingdom ................ 8512795

[51] Int. Cl.[4] .............................................. A61F 3/00
[52] U.S. Cl. .................................................... 128/80 F
[58] Field of Search ................. 128/80 C, 80 F, 80 R, 128/87 R, 88, 89 R; 623/38, 27

[56] References Cited

U.S. PATENT DOCUMENTS

| | | | |
|---|---|---|---|
| 552,143 | 12/1895 | Rankin | 128/80 F |
| 821,619 | 5/1906 | Drier | 128/88 |
| 1,007,567 | 10/1911 | Holder | 128/88 |
| 1,295,297 | 2/1919 | French | 128/88 |
| 1,418,283 | 6/1922 | Cameron | 128/80 F |
| 2,409,195 | 10/1946 | Crawford | 128/87 R |
| 2,573,715 | 11/1951 | Kelly | 128/89 R |
| 4,088,129 | 5/1978 | DiGiulio | 128/87 R X |
| 4,481,941 | 11/1984 | Rolfes | 128/80 C X |
| 4,602,627 | 7/1986 | Vito et al. | 128/80 C X |

FOREIGN PATENT DOCUMENTS

1184459  3/1985  Canada ............................. 128/87 R

Primary Examiner—Clifford D. Crowder
Attorney, Agent, or Firm—James & Franklin

[57] ABSTRACT

A modular bracing system has a relatively small number of elements adapted so that some or all of them may be easily connected to make a variety of braces for the lower limb in the first instance. Lateral and medial calf and thigh shells have central recesses along their entire inner surface with holes at regular pitches. Shells have embossed cut lines across their width to aid accurate fitting. Hip, knee and ankle hinges have arms with corresponding widths, thicknesses and holes so that they may be received intimately into the shell recesses in a variety of positions. By this means, the length of braces and orthoses so formed may be adapted for patients of widely varying height. Wraps made of thin foam covered with pile fabric are embossed with cutting patterns for easy customizing of the braces. Wraps lie under the appropriate shells to render the brace comfortable to wear without inducing relative movement between wearer and brace and the entire unit is secured in place with straps.

3 Claims, 7 Drawing Sheets

F I G. 1
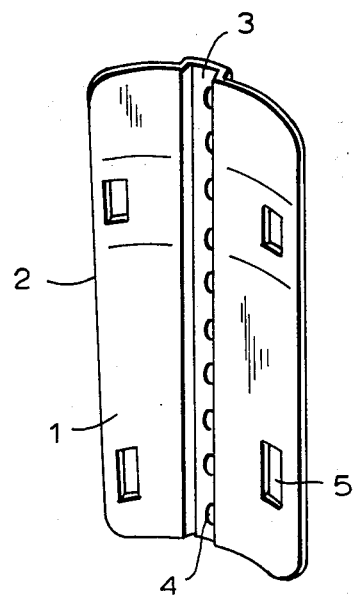
F I G. 2
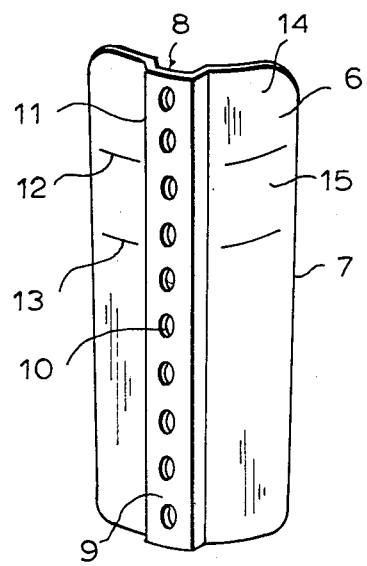
F I G. 3
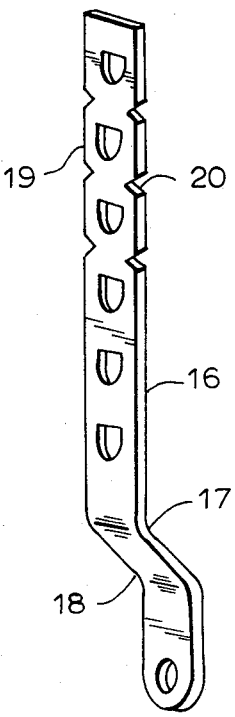

MODULAR LOWER LIMB BRACING SYSTEM

BACKGROUND TO THE PRESENT INVENTION—THE PRIOR ART

Bracing of the lower limb is widely employed in orthopaedics, sports medicine and physiotherapy. Many well known methods and techniques are used.

The construction of the brace naturally tends to be related to the intended function. Thus, when it is required to simply provide a degree of support to the musculature of the thigh, seamless elastic fabric sleeves of the type made by surgical hosiers are often used.

However, in the technique of cast bracing for fractures, much more structural integrity is needed in the brace. This technique was pioneered by Professor Augusto Sarmiento in the nineteen-sixties and seventies. Hinges were developed to make an articulation between a lower or tibial cast member and an upper or femoral cast member. For many years, only Plaster of Paris was readily available for making cast members. These tended to be heavy and had a long period of setting-to-weight-bearing. Plaster of Paris is also radio-opaque which precludes monitoring of the fracture with the brace in situ.

So-called new casting materials of two main types were introduced in the late seventies and early eighties. Both resin-impregnated bandages and low-temperature thermoplastic sheets overcame the disadvantages of Plaster of Paris and its derivatives but these materials did not bond very effectively with the headplates used in the early hinge designs.

By the end of the seventies, several designs of hinge for the ankle in metal and in plastic had been introduced. These included types referred to as heel cups and sold by the United States Manufacturing Company of Pasadena, Calif. and Camp International of various addresses including Winchester, England.

At least one hinge for the hip was on sale in Europe—the Hynabrace Hinge made by Messrs Blatchford's of Basingstoke, England and sold by Messrs Smith and Nephew of Hull, England. This device was indicated for proximal third femoral fractures.

In response to a perceived need for cast bracing hinges which would mate well with new casting materials, one of the present inventors (D.E.Y.) and D. H. Boyes developed a new kind of hinge headplate. This is described in published U.K. patent application GR No. 2130488, published European application EPN No. 0 109 847, U.S. Pat. Nos. 4,467,792 and 4,559,935.

The present authors have gone on to develop a novel ankle hinge and a novel hip hinge disclosed in U.K. application No. 8501613 and in U.S. application Ser No. 734,050. More recently, they have disclosed a new type of hinge mechanism for knee hinges in U.K. application No. 8510,028 and in U.S. application Ser. No. 853,962, now abandoned.

Hinges designed for use in cast bracing have never been restricted solely to that application and it has been a frequent practice for orthotists and orthopaedic technicians to build them into orthoses, with or without casting material. An example we have encountered is the construction of hip orthoses used in Legg-Calve-Perthes disease where cast brace knee hinges have been modified and used.

Hinges of this general type have also been used in orthoses for supporting and bracing ligament injuries. A good example of this is a hinge according to Lerman, described in U.S. Pat. Nos. 4,337,764 and 4,372,298 and sold by Zinco Industries of Montrose Calif. This hinge is sold by itself for cast bracing and for surgical knee ligament repairs which are clear orthopaedic indications. However, this hinge is also built into a knee control orthosis which has indications ranging from minor knee instabilities to the protection of repaired ligaments in closely monitored rehabilitation programmes.

The latter type of indication derives mainly from sports medicine which has increased in importance in recent years as more and more people in western civilisations take part in widely varying sports.

There is little doubt that the increasing number of knee ligament injuries in particular, which are now being seen in general orthopaedic clinics, derive substantially from the fact that older and less fit people are jogging, skiing, playing soccer, rugby, American football and other games, often at a competitive level.

In the United States, bracing of joints, especially the knee, is well developed. The Lenox-Hill derotation brace, introduced in the sixties, was almost certainly the first to achieve widespread use. This device is well reviewed in an article by James A. Nicholas, M.D. entitled "Bracing the Anterior Cruciate Ligament Deficient Knee Using the Lenox Hill Derotation Brace" which appeared in Clinical Orthopaedics and Related Research Number 172, January-February 1983, Pages 137 to 142.

We have surveyed the field of sports medical bracing in the U.S.A. and Europe and have identified 18 different types which are important by virtue of widespread use or because they embody some feature specific to themselves. All were of U.S. manufacture, few bore any indication that any of their features were patented or the subject of pending applications. A number of other types and makes were found but they did not appear to contribute any extra features to the art.

Braces can generally be compared via a series of common elements such as hinge mechanisms, hinge arms, means of terminating hinge arms, wraps, securing means and accessories.

Hinge mechanisms

We consider knee hinge mechanisms at some length in the early part of our U.K. application No. 8510028 and in our abandoned U.S. application Ser. No. 853,962. The following is an outline of such mechanisms in relation to the types of brace currently under review.

A few knee braces in common use employ single pivot hinge in which the hinge arms are united by the pivot. The ability of these hinges to track the motion of the knee joint is not very good since the knee joint is not a simple pivot joint.

This type of hinge is most frequently encountered in prophylactic sports supports. There are, however, three important braces which adopt modifications of this basic arrangement. The Feanny knee hinge by Medical Designs Inc has a single pivot which can move anteroposteriorly between limits in a slot. The limits are set by two screw adjusters which bear on the pivot via a spring cable. This hinge is described in U.S. Pat. No. 4,487,200.

Another type is the 3D brace 3D Orthopedic Inc of Dallas, Tex. which uses a single pivot hinge incorporating a series of concentric plates with segmental serrations over part of their surface by means of which adjustment for limited ranges of motion may be achieved.

A more recent variant uses a sprung peg in a serrated slot to control motion.

The Lenox Hill brace features a single pivot knee hinge mechanism in which the pivot moves along a curved slot of changing radius.

The majority of knee braces feature hinge mechanisms which have two pivots and are geared. This is to say that motion in the distal element of the hinge will produce motion in the proximal element. Such an arrangement is mechanically reliable but does not give very accurate joint tracking.

The most distinctive types in this category are those which use the Lerman hinge mentioned above. Adjustment is achieved by compression screws with nuts which may be positioned at any point along an arcuate slot in a plate to act as stops.

Some hinges used in knee braces have bi-pivotal mechanisms. In this type of hinge, each pivot can move independently, thus conferring an extra degree of freedom and better tracking of the instant centre pathway of the knee. The Anderson Knee Stabler made by Omni Scientific Inc of Lafayette, Calif. is a sports brace with a hinge of this type which has simple pivots spaced widely apart. At this extreme spacing, bi-pivotal hinges probably detract from rather than add to knee stability.

Ankle hinges used in the type of brace under consideration were found, without exception, to be single pivot types. Most manufacturers make no recommendations regarding the use of an ankle brace in conjunction with a knee brace. A few, however, make the reasonable observation that rotation in the affected knee is undesirable and suggest that tibial rotation may be limited by using an ankle brace to prevent inversion and eversion of this joint. For this limitation to be achieved, it is necessary to restrict the hinge to uniaxial motion.

None of the braces traced offered a hip hinge element.

Hinge arms

Hinge arms vary greatly in form. In most braces enjoying widespread use they are made of flat aluminium or steel bar. Some braces, especially those in which the hinge arms are used as gears in the hinge mechanism, employ press-blanked arms. Yet other braces employ short hinge-arm carriers to which other brace elements, such as a shell or band which passes anteriorly or posteriorly around the limb, are directly attached. A brace made by Medical Designs of Arlington, Tex., U.S.A. has metal arms with Velcro type hook covers. This would prevent its being used with conventional lateral and medial shells and suggests it would be unsuitable for use in leg fractures where instability could occur if the brace is built up according to the description in U.S. Pat. No. 4,407,276.

Means of terminating hinge arms

The types of brace under consideration are not used with casting materials and therefore do not have headplates. A few braces, such as the Bledsoe brace by Medical Technology Inc of Grand Prairie, Tex. have an analagous structure in the form of a pocket which slides intimately over the end of the hinge arms. This type of termination often has a loop and pile method (of the well known type sold as Velcro) of attachment to wraps which are bound around the limb before the hinged parts of the brace are fitted. In this respect, it is very similar to the Medical Designs device described in U.S. Pat. No. 4,407,276, the author of which is Bledsoe.

Many braces in this category have a hemicircumferential band, anterior or posterior to the limb, uniting the medial and lateral proximal hinge arms. A second similar band unites the corresponding distal hinge arms.

Many braces featuring anterior or posterior bands are nonadjustable. However, the Donjoy brace has a series of location holes in the bands. These allow screw fixings to be located in different positions so that varying limb circumferences may be accommodated.

In designs where adjustment for different circumferences cannot be made, there are often as many as 6 sizes left and right. This is highly disadvantageous to those supplying the brace who have to maintain a very large inventory.

Often, the anterior or posterior bands have pockets in or on them which accommodate the hinge arms; these are an alternative to the screw fixings used on the Donjoy brace.

Another popular method of terminating the hinge arms is with shells, usually made of plastic. These are basically thin curved sheets which extend around and beyond the ends of the hinge arms to which they are attached. Such shells are usually preformed so that when the brace is offered to a leg they already partially conform to the limb curvature. Shells of this type are used in the 3D brace and in this case they are recessed along part of their lengths to accept the ends of the hinge arms which are rivetted to them.

Wraps

Most manufacturers recognise that it is uncomfortable and thus unacceptable to have a brace strapped directly over the skin. Some simply suggest that a stockinette underlayer is used. Others provide foam wraps, usually with a fabric facing, which are first applied over the limb to be braced. The brace can then be fitted and strapped firmly in place without significant discomfort.

Wraps, of course, did not emerge with modern braces—the concept of 'comfort materials' provided for underlying orthotic and prosthetic components is very well established in most civilised Western countries and there appears to be a close morphological and structural relationship between underbrace wraps and underlayers used by armourers many centuries ago to make metal suits tolerable. This can easily be verified by casual study of many exhibits in the Tower of London and elsewhere. Certainly the concept of flexible padding sheets wrapped around the thigh and calf and attached to themselves seems to have been well developed by 1801 when Gavil Wilson used leather wraps under his splints, reproduced pictures of which we have in our possession.

U.S. Pat. No. 4,407,276 by Bledsoe includes in claim 1 (a) the statement that 'first and second flexible sheets of cushioned material, one of which is adapted for snugly wrapping around the wearer's calf, and the other being adapted for snugly wrapping around the wearer's calf, and the width of each sheet being sufficient to circumferentially envelope at least most of its associated leg member, and said sheets being selectively removeable and replaceable around the wearer's leg members.'

However, we have in our possession several examples of braces filled with such flexible sheets and meeting these criteria which were designed by a Canadian, Mr L Plewes, whilst working as a Consultant Orthopaedic Surgeon at the Luton and Dunstable Hospital, Bedfordshire, England in the early 1940's. Many thousands of these braces were used at this major hospital in the period up to Mr Plewes retirement a few years ago and some are still used today. Illustrations of this type of brace appeared in orthopaedic textbooks in the 1960's.

In some braces which are specifically indicated for the purposes of derotating the lower limb (this is to say that the tibia is derotated with respect to the femor), very intimate contact between the brace and the limb is aimed for. Hence, in the Lerman Multi Ligamentous Orthosis, broad rubber straps are used to grasp the limb very firmly over only a thin stockinette layer. This is apparently to try to ensure that pull on the limb in one direction, proximal to the hinge and pull in the opposite direction distal to the hinge, may be applied and will hopefully be maintained.

Our investigations on foam wraps in current use indicate that in general they are too thick to sustain the clockwise and counterclockwise pull, needed for derotation. When good contact is made with the patient beneath and the brace above, shear forces within the foam from which wraps are made cause it to yield against the pull. This manifests as relative motion between the inner and outer surfaces of the foam and reduction of torque.

The other consequences of thick foam wraps in prior art braces such as those used on the Medical Designs and the 3D are excessive bulk around the limb and discomfort caused by heat build-up.

Some manufacturers attempt to shape their wraps to assist in fitting limb shape. Such wraps are often provided with a loop and pile closure. In the 3D brace, where this type of wrap is supplied, we have found it necessary to offer the wrap to the limb from the wrong end in order to guess or assess the correct position for the tailored portion of said wrap. This type of arrangement does not make for ease of fitting.

Straps

Most braces are secured to the limb with straps which are either separate or are fixed to partial circumference bands or hinge arms. Separate straps typically pass right around the limb and both buckle-type securing means and loop and pile closures are popular.

The number of straps varies between 2 and 6, typically 1.5" or 2.0" wide. Both elastic and inelastic types are used.

Most straps are of the velcro type, the purveyors of this material having recognised it's value and promoted it for retaining bivalved casts and expanding jackets and cast for at least 10 years.

Knee Cages

Many braces feature some form of knee cage; sometimes the term 'condylar pads' is used for a substantially similar structure.

In some braces the knee cage is very rudimentary. For example, the Donjoy brace has a simple small oval plate with a foam liner attached pivotally on the inner aspect of each hinge. The plates cannot be linked together.

In other braces the cage is bigger and has more components. For example, the Lerman Multi Ligamentous Orthosis has larger shaped and lined condylar pads mounted on the inner aspect of each hinge. These are provided with a system of straps and buckles for linking the pads together and holding them in position at the knee once the brace is fitted.

Where a manufacturer states aims for a knee cage these are generally:

(a) The enhancement of medial and lateral stability of the knee.
(b) To prevent the brace from riding down the leg.
(c) Tracking the motion of the patella.

It is clear from first principles that any knee brace which does ride down the leg will fail to achieve any beneficial effect to the wearer.

Flexion and Extension Assist Devices

These are mainly of two types. The 3D brace uses coil springs secured around the hinge mechanism which tend to either close (flex) or open (extend) the hinge according to their shape and orientation. Accordingly, an exercise and assist function is introduced.

Other braces use additional straps of neoprene or elasticated fabric across the knee joint to achieve the same end.

Other Features

Some braces have additional features. The most important are probably cross-knee straps which are generally called valgus or varus correction straps. They are intended to introduce forces which oppose the inward or outward angulation of the limb, respectively.

Some braces, for example the Bledsoe and 3D which have, respectively, shell and pocket type terminations of the hinge arms, do not require to be sized for different leg circum-ferences. However, they are offered in sizes to cater for varying limb lengths. This still leaves the supplier with the problem of having to hold a large inventory in order to be reasonably sure of being to fit any patient who may require a brace.

AIMS OF THE PRESENT INVENTION

It is the primary aim of the present invention to provide a modular system of braces and brace components for the lower limb sufficient to construct orthoses and braces for the knee joint, the ankle joint and the hip joint or combinations of these joints and the upper and lower leg.

It is another aim of the present invention that the modular system should be comprised of a small number of simple interconnecting components presented in a single kit form or in a single pre-assembled form for each joint, combination of joints or portion of the leg to be braced.

It is another aim of the present invention that the components of the modular system should be so sized and configured as to allow the person fitting braces constructed therefrom to accommodate most potential wearers, regardless of limb length or circumference, from a single size kit or single pre-assembled form for each joint, combination of joints or portion of the leg to be braced.

It is another aim of the present invention that the modular system should be so configured as to be widely adaptable for uses ranging from sports applications to conventional orthopaedic indications with good structural and functional suitability in all areas.

It is yet another aim of the present invention that the modular bracing system should be easy to fit in the first instance and thereafter be easy to put on and take off.

OUTLINE OF THE PRESENT INVENTION

The present invention relates to a modular lower limb bracing system for externally bracing the ankle, knee and hip joints singly and in combination, as well as the upper and lower leg. The term modular is used to indicate that a number of common parts are used from which a variety of different braces can be constructed.

According to one aspect of the present invention, there are provided flexible plastic plates, hereinafter referred to as shells. Said shells are trapezoid and curved, having a shape as would be achieved by cutting a trapezium from the surface of a hollow cylinder. Each shell has a central recess formed along the full length of the concave surface. This recess is an adaptation to receive hinge arms from either end.

Holes are provided at regular intervals along the recess and these correspond with holes in the hinge arms. The holes in shell and hinge arm elements are aligned so that they may be secured together by suitable fixing means such as nuts and bolts.

Shells are conveniently made by vacuum forming or injection moulding. Their curved surfaces assist in fitting to the limb.

The shell used on the lower leg is long relative to its width. It is wider at the top or proximal end than at the bottom end. The shell used on the upper leg is wider and shorter than the tibial shell. In use, shells are fitted to hinge arms and are fitted on the medial and lateral aspects of the limb over wraps to protect the skin of the limb from contact with metal and plastic components.

Shells having a full length recess according to the present invention are the means of uniting hip, knee and ankle hinges for the joint or combination of joints to be braced. Said full length recess, in combination with the series of fixing holes along it and the corresponding holes in the hinge arms, provides means for elongating a brace.

According to another aspect of the present invention, both tibial and femoral shells are embossed with cut-lines across them so that they may be readily trimmed down to a correct size (using scissors or a knife) if a short brace is required.

According to another aspect of the present invention, femoral shells have slots formed across the central recess. This is an adaptation for receiving hip hinge arms. When a hip hinge is used, it may be required to have the shell high on the lateral aspect of the limb. If only the central recess were available and the hinge arm were offset, the height to which the shell could be raised might not be sufficient. The provision of said slots allows it to be raised higher.

According to another aspect of the present invention, hip, knee and ankle hinges have arms, which are preferably made in a suitable aluminium alloy, adapted by having cutting guides marked across them. Said guides may conveniently be 'y' shaped notches punched in each edge of the arms at the mid-points between fixing holes. The length of the arms may be reduced, if required, by cutting them through at the guide marks with a small hacksaw.

The full length recess, in combination with embossed cut-lines on shells and cut markings on the hinge arms, constitutes means of making a short brace.

Combination of these features thus provides a bracing system which, from one set of tibial and femoral shells, together with hinges having arms with cutting guides, will fit a wide range of leg lengths. Furthermore, said bracing system is independent of the circumference of the upper and lower leg.

It will be appreciated that it is not always required to brace the entire limb at one time, frequently only one joint being treated or protected. The instant system provides a series of modules using the common components of shells and hinge arms with a specific hinge for each joint. Thus an ankle or tibial brace will employ a pair of ankle hinges (having medial and lateral hinge arms) and a pair of tibial shells. A knee brace will employ a pair of knee hinges plus pairs of tibial and femoral shells. A hip brace will employ a hip hinge and femoral shells.

The system is especially valuable where combination braces are required, such as in a so-called full-leg orthosis which combines a knee brace with an ankle brace. Using the instant invention, one pair of femoral shells is used with one pair of knee hinges, one pair of tibial shells and a pair of ankle hinges.

As previously discussed, any limb circumference may be fitted from a single set of components. Furthermore, using shells and hinge arms according to the present invention, leg lengths varying by 1641 can readily be accommodated by a single full set. Put differently, if the assembled complete brace fits a person of 5' 8" in height with the hinge arms in the mid position in the shells, the brace may be adjusted for user heights which will probably exceed 6' 5" down to probably less than 4' 11".

According to another aspect of the present invention, there is provided a series of fabric-faced foam wraps over which the shell, hinge arm and hinge components, hereinbefore described, are secured by means of broad loop and pile straps of the kind sold as Velcro.

Said wraps are fitted right around the circumference of the limb. Femoral and tibial wraps correspond to the femoral and tibial shells. In addition, knee and ankle wraps are provided as well as a hip pad.

Wraps according to the present invention accommodate wide variations in upper and lower leg circumferences and also allow for the possibility that shells will need to be reduced in length during use.

Femoral, tibial, knee and ankle wraps are basically arcuate in form. In femoral and tibial wraps, the arc is somewhat broader than the length of the corresponding shell. The length along the arc is adequate for the largest limb circumference likely to be encountered in ordinary use. Radial cut-lines are embossed into the wrap at convenient intervals from one end, such that the last cut-line leaves a length which corresponds to the smallest limb circumference likely to be encountered in ordinary use. To produce a wrap of the correct length, the uncut version is first placed firmly around the limb. The amount of overlap needed to achieve secure fixing without excess is then easily seen and the surplus is cut away along the appropriate embossed lines.

Additional cut-lines are embossed into the fabric some way in from the top and bottom margins. These are to allow the wrap to be trimmed down if the shells are shortened.

The provision of embossed cut-lines on the wraps ensures that a customised wrap appropriate to the wearer may be produced without risk of damage through excessive or incorrect cutting. They also preserve the cosmetic appearance of the wraps and ensure that fraying of the facing material does not occur.

Knee and ankle wraps do not correspond directly with a shell. Both these wraps conform to the general pattern hereinbefore described for tibial and femoral wraps and can be shortened both in length and breadth. However, in addition, the knee wrap has an embossed patella cover which may may be left in situ or cut away as required. The ankle wrap is embossed distally to provide trimmable malleolar pads and a trimmable instep area.

DESCRIPTION OF PREFERRED EMBODIMENTS

In order that the present invention may be more readily understood, reference will now be made to the accompanying drawings of a preferred embodiment in which:

FIG. 1, shows a perspective of the inner surface of a tibial shell with a full length recess.

FIG. 2, shows a perspective of the outer surface of a femoral shell with slots and embossed cut lines.

FIG. 3, shows a perspective view of a hinge arm with cutting guides.

Figure 4:
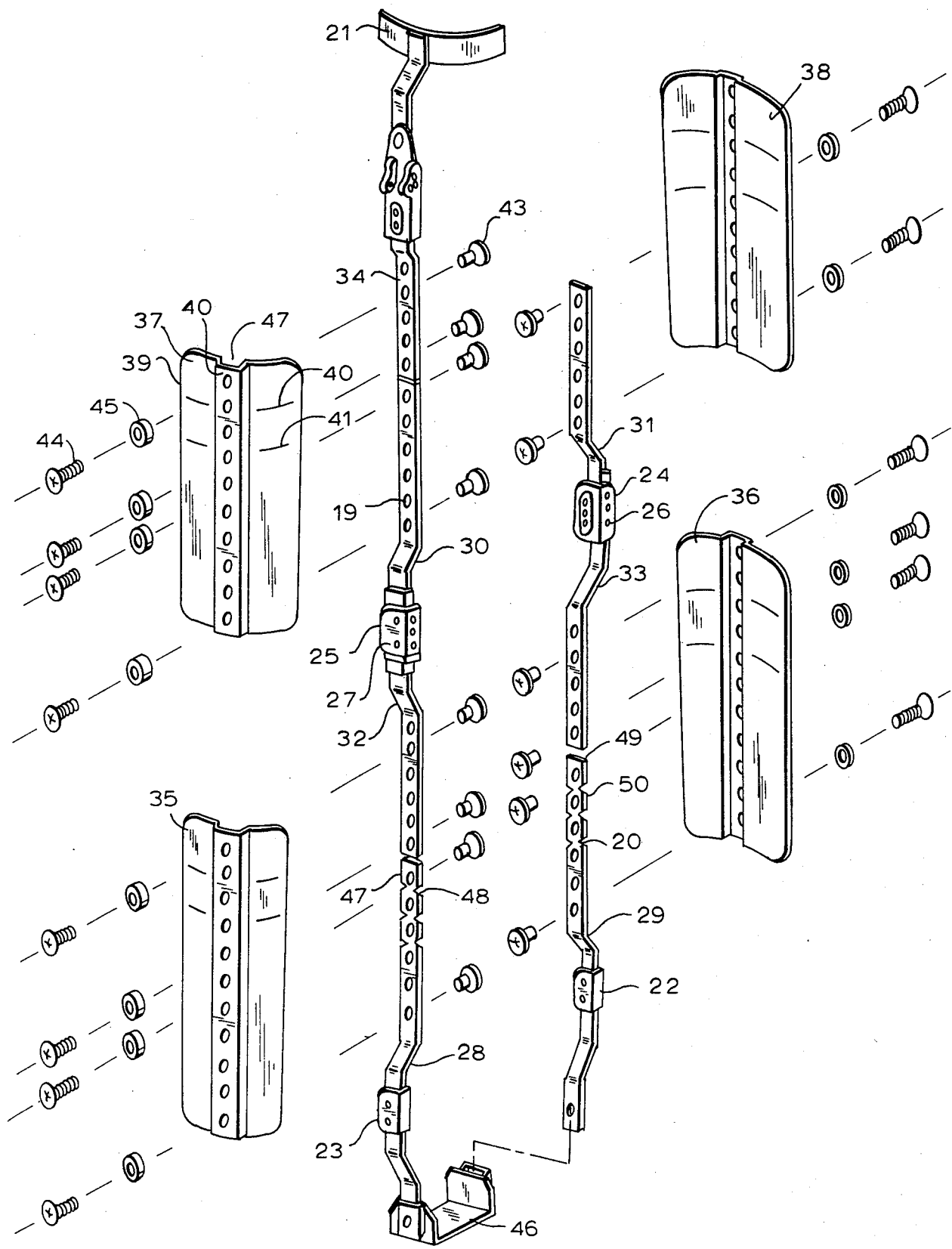
FIG. 4, shows an exploded view of a knee brace to indicate how shells and hinge arms are mutually attached.

Considering first FIG. 1, in which the inner surface 1, of a tibial shell element 2, of a modular lower limb bracing system is shown in perspective. Tibial shell 2, is conveniently formed in plastics, such as nylon, by injection moulding or vacuum forming to an inwardly curved shape. The purpose of the curved shape and the use of a flexible material is to make the shell conform readily when incorporated into a brace and strapped onto the limb.

Tibial shell 2, is formed with the general plan shape of a trapezium cut from the surface of a cone. The length is adequate to extend over most of the length of the tibial shaft in persons over 6 feet tall and of regular proportions. The width at the top and bottom should be unlikely to exceed half the circumference of the lower leg just below the tibial tubercule and just above the medial malleolus respectively in persons 5 feet tall and of regular proportions.

Tibial shell 2, is shaped so that it will seat readily on either the medial or lateral aspect of the lower leg when applied over a suitable underwrap.

A central groove or recess 3, extends the full length of the inner surface. Holes 4, are formed at regular intervals along the central recess 3. Self-adhesive Velcro patches 5, are applied at several points on inner surface 1.

Turning now to FIG. 2, there is shown the outer surface 6, of a femoral shell 7, which is similar in all important respects to the tibial shell 2, hereinbefore described except that it is proportionally broader at top and bottom to fit more adequately on the greater circumference of the thigh. A central recess 8, is reflected on the outer surface 6, as a raised central portion 9, extending along the whole length and having holes 10, spaced regularly along it of the same diameter and centres as holes 4, in tibial shell 2, of FIG. 1.

Slots 11, extend across and through the upper or proximal section of raised central portion 9, spaced midway between the centres of holes 10. Embossed cut lines 12 and 13, de-lineate areas 14 and 15, of femoral shell 7, which may be cut away with shears or heavy duty scissors if it is required to shorten the shell to make it fit persons with short femors.

There is no feature analogous to slots 11, in tibial shell 2, in the preferred embodiment, however embossed cut lines are present to enable short tibias to be accommodated. Velcro patches are used on the inner, non-illustrated surface of femoral shell 7.

The length of femoral shell 7, is adequate to extend over most of the length of the femoral shaft in persons over 6 feet tall and of regular proportions. The width at the top and bottom should be unlikely to exceed half the circumference of the upper leg just below the groin flexure and just above the femoral condyles respectively in persons 5 feet tall and or regular proportions.

Turning now to FIG. 3, there is shown a hinge arm 16, of the type used for knee hinges, as the lower hinge arm on a hip hinge and as the upper arms on ankle hinges. In the preferred embodiment, hinge arm 16, has offsets 17 and 18, to step hinge mechanisms off from the joint or joints being braced, however, we also contemplate hinge arms which are flat. Holes 19, are pitched at the same centres as holes 4 and 10, in the tibial shell 2 and femoral shell 7, of FIGS. 1 and 2, respectively. Cutting guides 20, conveniently in the form of 'y' shaped notches are provided midway between holes 19, to enable short braces to be constructed in conjunction with cut down shells as hereinbefore described.

Hinge arms according to FIG. 3, are preferably formed in aluminum alloy, although the use of mild steel and stainless steel is also contemplated and we have made examples in these materials. A single standard length and a single standard offset are preferred as these features confer maximum reduction in the number of parts employed in the modular system. However, increased versatility may be introduced by using a limited variety of offsets, such as 0.5", 0.75" and 1.25" which would substantially reduce any requirement for on-site bending of hinge arms which might otherwise be necessary to get good conformity to the limb taper in some users. The length of hinge arms according to FIG. 3, is such that when fitted to hinges and appropriate shells in the middle of the range of possible adjustment positions, the brace resulting should be suitable for persons of 5" 6" to 5' 8" of regular proportions.

In order that the method of brace construction and adjustment may be readily understood, reference will now be made to FIG. 4, in which an exploded view of a hip, knee and ankle brace is shown. We employ the convention of dotted lines to indicate the relationship between small parts and fixing holes.

A hip hinge 21, generally according to the principles of our pending U.K. application 8501613 and our pending U.S. application Ser. No. 734,050, is the proximal element in the brace of FIG. 4. Although this is normally used with a waist belt and shoulder harness, this is omitted from FIG. 4, since it is not essential to the instant arguments. The distal element of the brace is a pair of ankle hinges 22 and 23. The middle portion of the brace uses a pair of knee hinges 24 and 25, with adjustable hinge mechanisms 26 and 27, according to our pending U.K. application 8510028 and our abandoned U.S. application Ser. No. 853,962.

Upper ankle hinge arms 28 and 29, knee hinge arms 30, 31, 32, 33 and lower hip hinge arm 34, are all made according to the principles hereinbefore described in relation to FIG. 3 and unless otherwise stated, any discussion of hinge arms relates only to these. For the sake of clarity, cutting guides 20, are only numbered on upper ankle hinge arms 28 and 29.

In the hinge arms of the preferred embodiment of FIG. 4, the holes 19, given a general label only on upper knee hinge arm 30 and lower hip hinge arm 34, are flat on one side and are thus, effectively, 'D' shaped.

Tibial shells 35 and 36 and femoral shells 37 and 38, exhibit all the features described in relation to FIGS. 1 and 2. Fitting a brace of this type can be commenced from the foot or the hip using the ground or the waist as a fixed point of reference to establish the overall length required.

With, say, the hip hinge 21, fitted correctly on the waist, lateral knee hinge 25, is offered to the knee so that the midpoint of hinge mechanism 27, lies over the knee axis. It will immediately be established whether there is an overlap between the lower hip hinge arm 34 and upper knee hinge arm 30. When overlap is seen, it is necessary to trim one hinge down; this procedure is hereinafter described, however, in FIG. 4, it is clear that there is no overlap in the hinge arms under discussion.

Femoral shell 37, is now offered up so that it seats over the lateral mid-thigh region. At this point, it will be clear whether the lower margin 39, of femoral shell 37, will overrun the lateral femoral condyle. If so, the shell must be shortened by cutting along whichever of the embossed cut-lines 40 or 41, is appropriate or even between them if necessary. The central recess 42, of femoral shell 37, is now fitted over hinge arms 30 and 34 and the fixing holes 19, giving the best fit are selected.

An explanation of why we adopt bi-pivotal hinges in the preferred embodiment is pertinent at this point. Because the two pivots are spaced apart, they generate a wide 'envelope' of knee-following motion. This makes their positioning proximo-distally less critical than with other types of hinge. The pitch between pivots in the preferred bi-pivotal hinges is similar to the pitch between holes 19, in the hinge arms of the instant brace and the motion envelope is sufficiently large to accept the maximum compromise imposed by the hinge arms without significant loss of knee-tracking performance.

'D' shaped bushes 43, engage holes 19, in all hinge arms. Countersunk screws 44, are accepted into countersunk seats 45, which pass through holes 10, in femoral shell 37 and into bushes 43. By these means hinge arms 30 and 34, are assembled to femoral shell 37 and they are also the general means of assembly of all shells to hinge arms.

Lateral ankle hinge 23, attached to stirrup foot-piece 46, is offered up to the tibia. Since lateral knee hinge 27, is already in position, it will immediately be seen whether there is any overlap between hinge arms 28 and 32.

It can be seen that in FIG. 4, this was the case and that top section 47, of upper ankle hinge arm 28, has been sawn through at cutting guide 48. Ankle hinge 23, is now assembled to knee hinge 25 and tibial shell 35, using bushes 43, countersunk screws 44 and seats 45.

The medial elements of the brace, knee hinge 24, femoral shell 38, tibial shell 36 and ankle hinge 29, are then assembled in the same way as the lateral elements using bushes 43, countersunk screws 44 and seats 45.

The lateral elements are assembled in the same relative positions as the medial elements and obviously, top section 49, of upper hinge arm 29, would also be cut through at cutting guide 50.

Figure 5A:
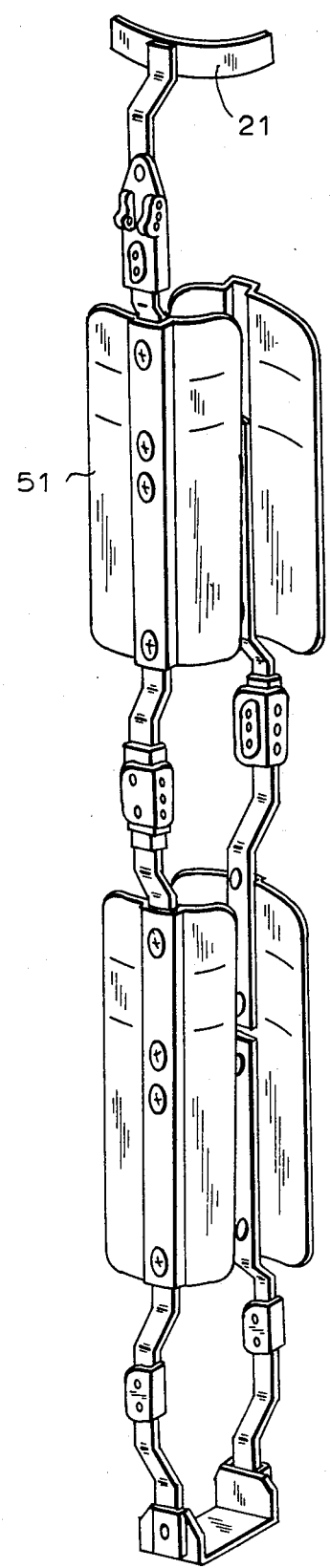
FIG. 5, shows a perspective of the types of brace which can be constructed from the bracing system.
Figure 5B:
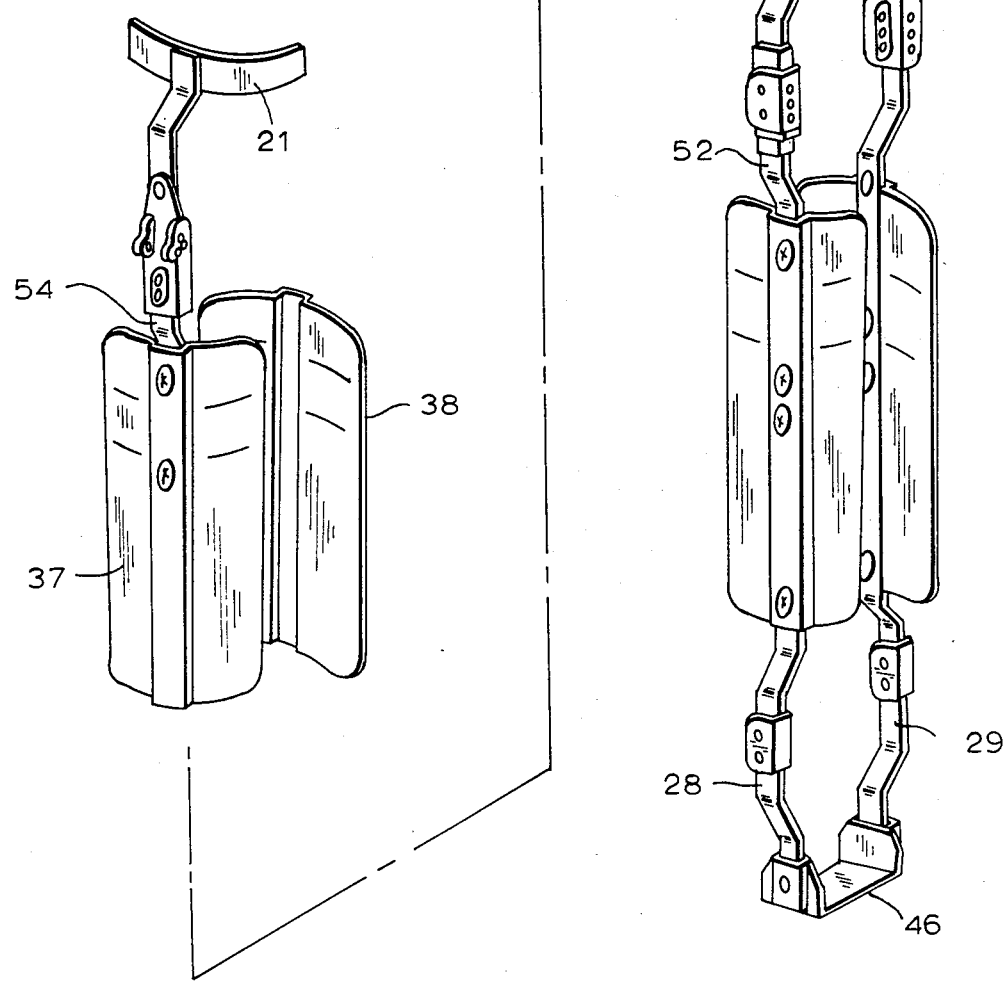
Figure 5C:
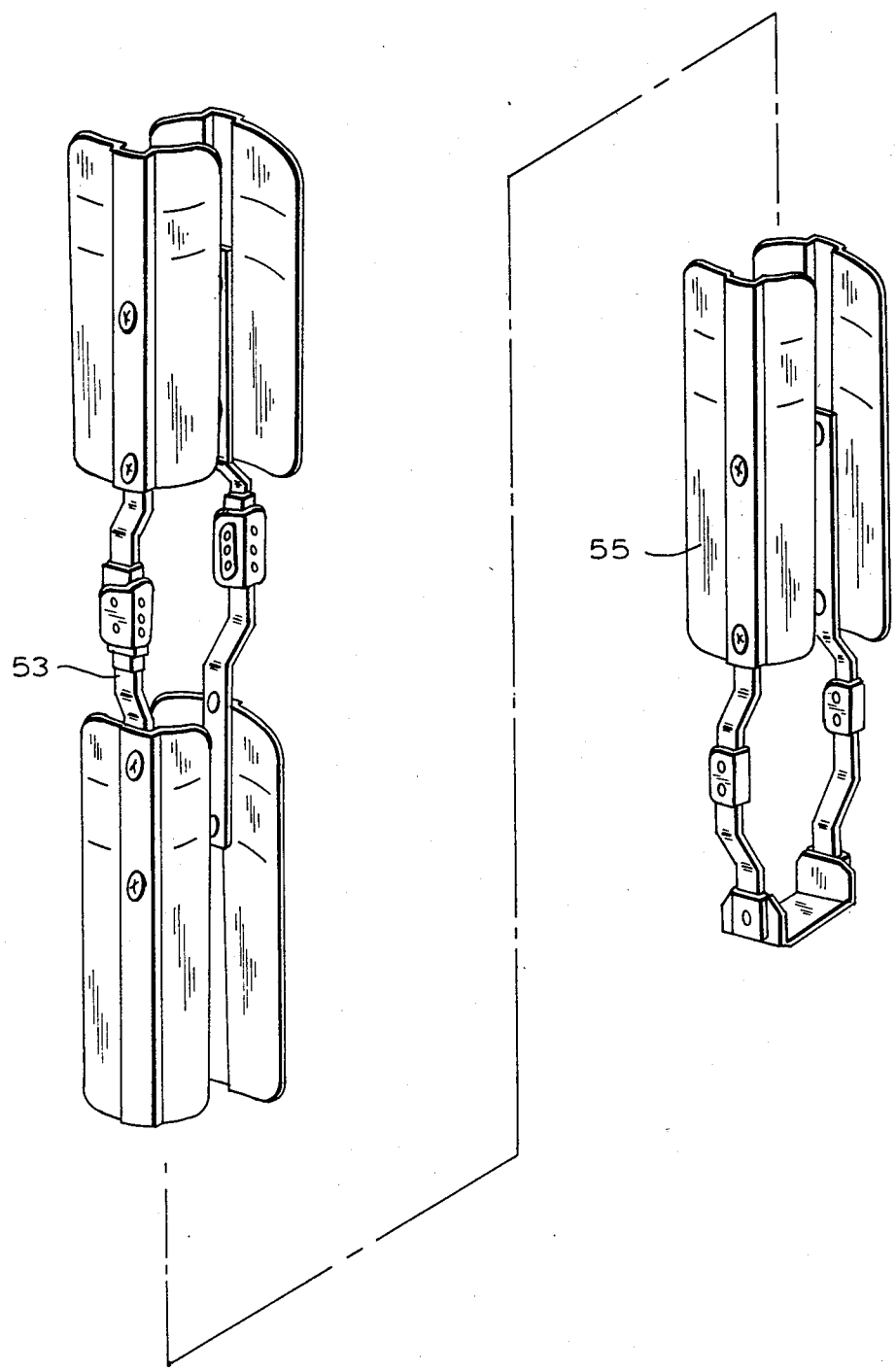

The potential of the bracing system can now be appreciated by reference to FIG. 5. The largest combination of parts is a hip, knee and ankle brace 51, previously considered in detail in relation to FIG. 4. Omission of hip hinge 21, leaves a knee ankle brace 52. Removal of the pair of ankle hinges 28 and 29, together with stirrup foot-piece 46, leaves a knee brace 53. The hip hinge 21, together with two femoral shells 37 and 38, constitutes a hip brace 54. The pair of ankle hinges 28 and 29, with stirrup foot-piece 46 and tibial shells 35 and 36, is an ankle or tibial brace 55.

Figure 6:
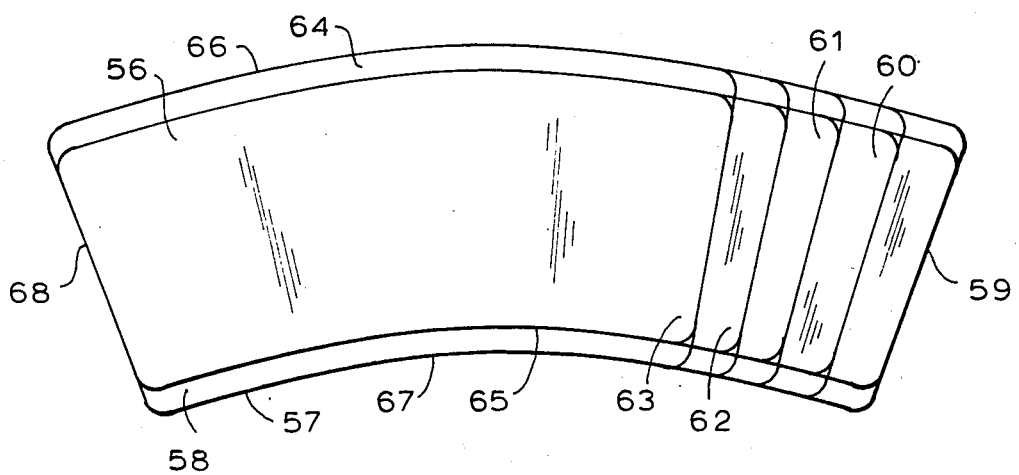
FIG. 6, shows a plan view of a femoral wrap to illustrate the feature of embossed cut lines.

It would clearly be uncomfortable to wear any of the braces of FIG. 5, directly over the skin and special wraps are used in the preferred embodiment. FIG. 6, shows a thigh wrap 56, according to the general principles of the present invention, in which a foam backing layer 57, has a bonded facing 58, of pile fabric which is Velcro attachable. The general shape of wrap 56, is arcuate and is formed in a heated press with the upper and lower edges corresponding to large radii. By means of this shaping, the wrap is easy to overlay onto itself without any significant tendency to 'run out', even on limbs which have a marked taper. Near one end 59, the wrap 56, is deeply embossed with a series of broad radial lines 60, 61, 62 and 63, spaced regularly apart. Further embossed lines 64 and 65, are set in from the top edge 66 and bottom edge 67, respectively. On the underside (not shown) at the opposite end 68, is a substantial area of Velcro hook. A tibial wrap, ankle wrap and knee wrap are also used in the bracing system, all constructed to the same basic principles immediately hereinbefore described.

Figure 7:
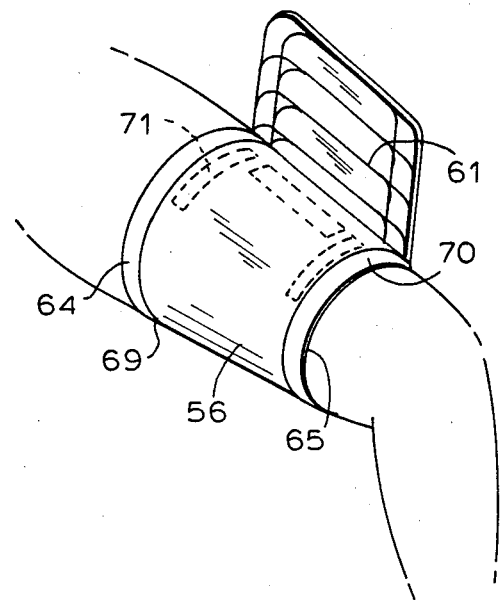
FIG. 7, illustrates the method of offering the femoral wrap to the limb for gauging the length which is appropriate and is representative of the general method for all wraps.

In FIG. 7, there is shown the general method for correctly sizing wraps, described in relation to the thigh wrap of the preferred embodiment.

A thigh wrap 56, is placed on a thigh 69, with the Velcro end 70, applied first. Velcro is indicated in hidden detail at 71. An embossed line is selected which will give an adequate but not excessive overlap when the wrap is in normal use. In FIG. 7, embossed line 61, would be used and the excess wrap is cut away along this line with scissors. In the example illustrated, there is clearly no requirement to shorten the wrap 56, proximo-distally, however, when this is necessary, it is cut away along embossed line 64, or 65, or both.

Figure 8:
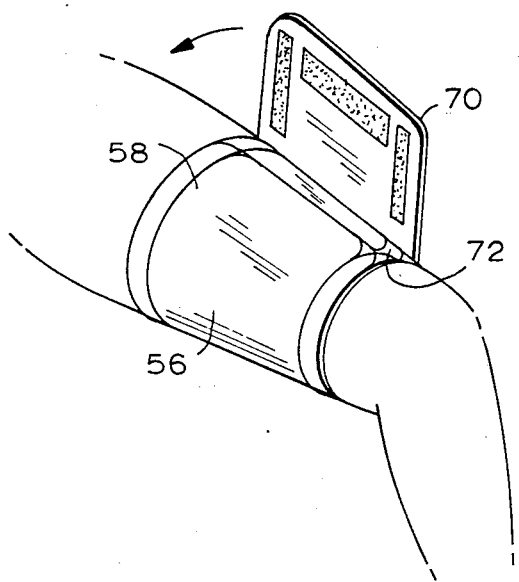
FIG. 8, illustrates how fitting of a customised thigh wrap is completed and is representative of the general method for all wraps.

In FIG. 8, there is shown the completion of fitting of the now individually tailored or customised thigh wrap 56. After trimming, wrap 56, is removed from the thigh and re-applied embossed end 72, first. Velcro end 70, is then firmly pressed onto velcro attachable facing 58, as indicated by the arrow.

Figure 9:
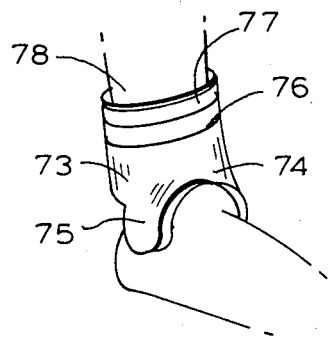
FIG. 9, shows how the principle of the embossed wrap is extended in the ankle wrap for fitting around the instep and malleoli.

FIG. 9, shows an ankle wrap 73, in situ. This wrap is sculptured near the lower edge 74, so that it will more readily fit over the instep and to provide padding over the malleoli. An embossed line 75, allows the lower part of ankle wrap 73, to be customised for varying sizes of ankle. In this instance, embossed lines 76 and 77, for proximal shortening are both inset from the proximal border 78. Apart from these details, the ankle wrap is generally similar to other wraps which are not illustrated.

Figure 10:
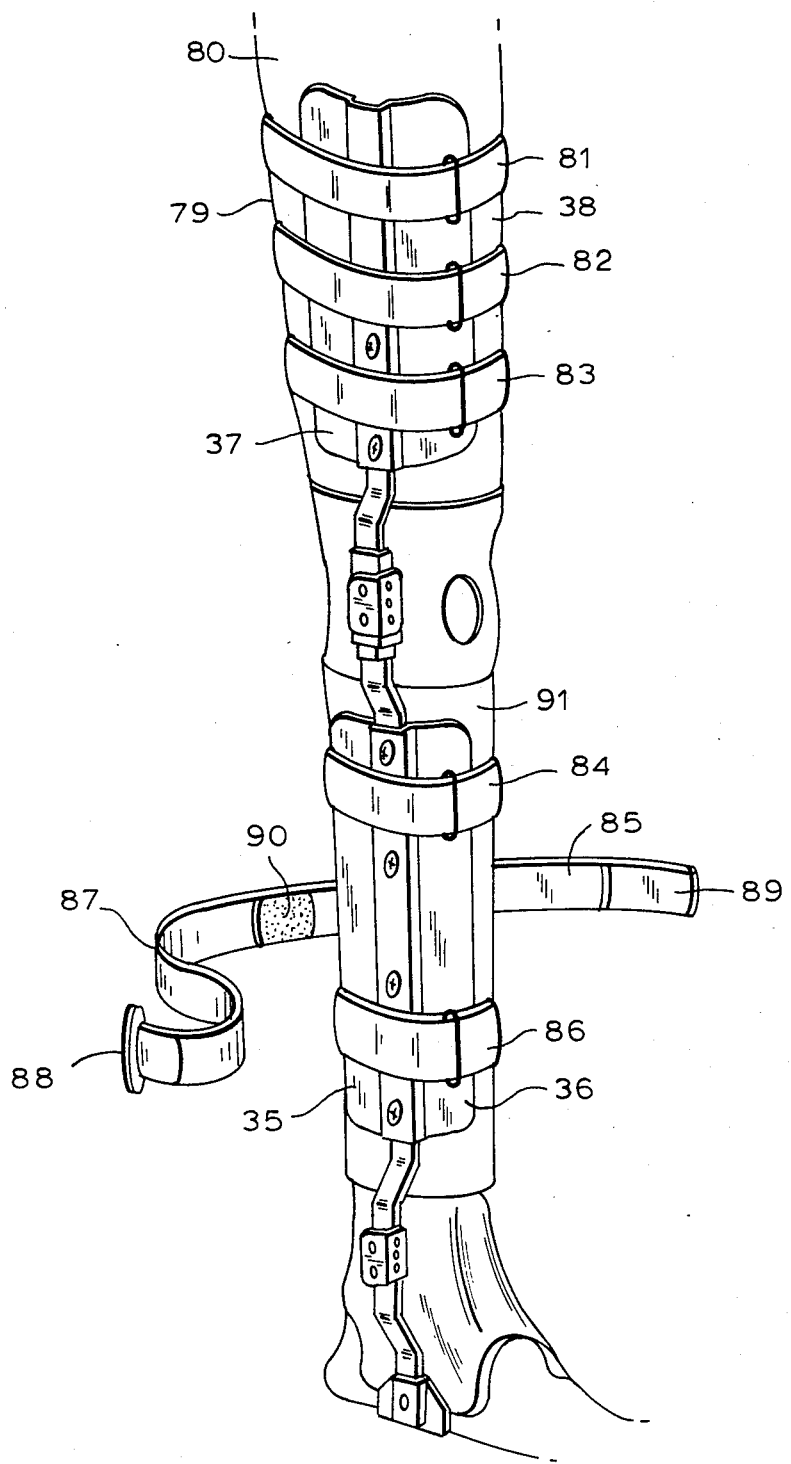
FIG. 10, shows a knee brace, complete with wraps and straps, fitted on a leg.

FIG. 10, shows a combined knee and ankle brace 79, in position on a leg 80. Broad velcro straps 81, 82, 83, 84, 85 and 86, are substantially similar to one another, although tibial straps 84, 85 and 86 are conveniently somewhat shorter than femoral straps 81, 82 and 83. It will be seen that because said straps cover a large proportion of the area of shells 35, 36, 37 and 38, brace 79, is very well secured to leg 80.

Tibial strap 85, is shown ready to be fitted, as a general example of strap construction. It consists of a length of pile Velcro 87, attached to a slip ring 88, conveniently achieved by sewing or high frequency welding. At the other end is attached a short section of loop velcro 89, with the loop surface facing outwards. A second short section of loop velcro 90, is fixed onto strap 85, with the loop surface facing inwards. Because shells 35, 36, 37 and 38 do not pass entirely around the circumference of leg 80, areas of femoral wrap 56 and tibial wrap 91, are exposed on the anterior and posterior surfaces.

The hook portion of strap 85, is pressed onto the exposed posterior surface (not seen in FIG. 10) of tibial wrap 91. Strap 85, is then passed around leg 80, and velcro loop section 89, is fed through slip ring 88. Velcro loop section 89, is then pulled tight, making sure that the blood circulation in the leg is not restricted. Loop section 89, is finally pressed onto pile section 87, to secure the strap. The same method of attachment applies to all other straps.

We contemplate the use of and have built braces according to the present invention with knee cages constructed using methods well known in the art, said knee cages are attached by screws to the inner surfaces of hinge mechanisms.

In another preferred embodiment, we employ knee hinges of a type designed by the present authors, manufactured by Proteclair Limited of Stokenchurch, Buckinghamshire, U.K. and sold by Messrs Seton Products Limited, Oldham, Lancashire, U.K.

We also contemplate braces built from components constructed according to the general principles disclosed herein, for use on the upper limb. In these braces, the shells and wraps used are somewhat smaller and hinge arms are shorter.

Whilst only a limited number of preferred embodiments of the present invention have been disclosed herein for purposes of illustration, it is obvious that many variations and modifications could be made thereto. It is intended to cover all of these modifications and variations which fall within the scope of the present invention, as defined by the following claims.

We claim:

1. A modular system of external bracing apparatus for the lower limb comprising: first and second pairs of curved shells adapted to be applied to the lateral and medial aspects of the calf and thigh respectively, each of said shells having a central recess formed along the entire length thereof, with a multiplicity of substantially regularly spaced discrete holes; hinge means with arms having widths and thicknesses substantially the same as the width and depth of said recesses such that said arms may be intimately received within said recesses; said arms having a multiplicity of discrete holes adapted to receive non-rotatable, selectively removable securing means therein, said holes in said recesses being of such dimensions that when said holes in said arms are aligned with said holes in said recesses, non-rotatable selectively removeable securing means are adapted to pass through said holes in said recesses and through said holes in said arms aligned therewith so as to retain said arms in said recesses, and first and second shaped resilient circumferential wraps for the thigh and calf respectively and lying under said shells.

2. The modular system of external bracing apparatus of claim 1 wherein each wrap comprises cutting patterns marked upon the outward facing surface thereon thus providing guides for individual tailoring of said wraps to patients.

3. The modular system of external bracing apparatus of claim 1 wherein each of said arms is secured to a respective shell by at least two sets of said non-rotatable selectively removable securing means so as to provide positive locking means between components.

* * * * *